(12) United States Patent
Van Dael et al.

(10) Patent No.: US 10,520,452 B2
(45) Date of Patent: Dec. 31, 2019

(54) AUTOMATED QUALITY CONTROL AND SELECTION

(71) Applicants: KATHOLIEKE UNIVERSITEIT LEUVEN, Leuven (BE); UNIVERSITEIT GENT, Ghent (BE); UNIVERSITEIT ANTWERPEN, Antwerp (BE)

(72) Inventors: Mattias Van Dael, Brussels (BE); Pieter Verboven, Herent (BE); Bart Nicolaï, Heusden-Zolder (BE); Jelle Dhaene, Ghent (BE); Luc Van Hoorebeke, Ghent (BE); Jan Sijbers, Duffel (BE)

(73) Assignees: KATHOLIEKE UNIVERSITEIT LEUVEN, Leuven (BE); UNIVERSITEIT GENT, Ghent (BE); UNIVERSITEIT ANTWERPEN, Antwerp (BE)

( * ) Notice: Subject to any disclaimer, the term of this patent is extended or adjusted under 35 U.S.C. 154(b) by 349 days.

(21) Appl. No.: 15/558,671

(22) PCT Filed: Mar. 16, 2016

(86) PCT No.: PCT/EP2016/055718
§ 371 (c)(1),
(2) Date: Sep. 15, 2017

(87) PCT Pub. No.: WO2016/146703
PCT Pub. Date: Sep. 22, 2016

(65) Prior Publication Data
US 2018/0113083 A1 Apr. 26, 2018

(30) Foreign Application Priority Data
Mar. 16, 2015 (GB) .................................. 1504360.7

(51) Int. Cl.
*G01N 23/046* (2018.01)
*G01N 33/02* (2006.01)
(Continued)

(52) U.S. Cl.
CPC ............ *G01N 23/046* (2013.01); *G01N 23/18* (2013.01); *G01N 33/025* (2013.01); *G06T 7/001* (2013.01);
(Continued)

(58) Field of Classification Search
CPC .... G01N 23/046; G01N 23/18; G01N 33/025; G01N 2223/419; H04N 13/204;
(Continued)

(56) References Cited

FOREIGN PATENT DOCUMENTS

EP 0875751 A1 11/1998
EP 1808813 A2 7/2007
(Continued)

OTHER PUBLICATIONS

Haff et al., "X-Ray Detection of Defects and Contaminants in the Food Industry," Sensing and Instrumentation for Food Quality and Safety, vol. 2, No. 4, Dec. 2008, pp. 262-273.
(Continued)

*Primary Examiner* — Michael C Bryant
(74) *Attorney, Agent, or Firm* — Workman Nydegger

(57) ABSTRACT

A non-destructive inspection method for inline inspection of an object comprises moving an object in between a radiation source and an image detector and through a three-dimensional scanner field of view, imaging the object using the image detector to obtain a projection radiograph of an internal structure of the object, scanning an exterior surface of the object using the 3D scanner, fitting a shape model of the object to a point cloud provided by the 3D scanner to obtain a surface model of the exterior surface, creating a solid model of the surface model by taking a grey value
(Continued)

distribution of a reference object into account, simulating a reference radiograph from the solid model and comparing the reference and projection radiographs to detect internal deviations of the object.

20 Claims, 4 Drawing Sheets

(51) Int. Cl.
    *G06T 7/00*     (2017.01)
    *G01N 23/18*     (2018.01)
    *H04N 13/204*     (2018.01)

(52) U.S. Cl.
    CPC ..... *H04N 13/204* (2018.05); *G01N 2223/419* (2013.01); *G06T 2207/10028* (2013.01); *G06T 2207/10081* (2013.01); *G06T 2207/10124* (2013.01); *G06T 2207/30128* (2013.01)

(58) Field of Classification Search
    CPC .......... G06T 7/001; G06T 2207/10028; G06T 2207/10124; G06T 2207/30128; G06T 2207/10081
    See application file for complete search history.

(56) References Cited

FOREIGN PATENT DOCUMENTS

WO      2010091493 A1      8/2010
WO      WO-2010091493 A1 *      8/2010      ............... G01N 9/24

OTHER PUBLICATIONS

Heimann et al., "Statistical Shape Models for 3D Medical Image Segmentation: A Review," Medical Image Analysis, vol. 13, 2009, pp. 543-563.
International Search Report From PCT Application No. PCT/EP2016/055718, dated Jul. 5, 2016.
Iovea et al, "Pure Translational Tomography—A Non-Rotational Approach for Tomographic Reconstruction," EC NDT, Jan. 2006, 5 Pages.
Jiang et al., "An Adaptive Image Segmentation Algorithm for X-Ray Quarantine Inspection of Selected Fruits," Computers and Electronics in Agriculture, vol. 60, 2008, pp. 190-200.
Johansson et al., "Automated Knot Detection for High Speed Computed Tomography on *Pinus sylvestris* L. and *Picea abies* (L.) Karst. Using Ellipse Filling in Concentric Surfaces," Computers and Electronics in Agriculture, vol. 96, 2013, pp. 238-245.
Mery et al., "Automated Fish Bone Detection Using X-Ray Imaging," Journal of Food Engineering, vol. 105, 2011, pp. 485-492.

* cited by examiner

AUTOMATED QUALITY CONTROL AND SELECTION

FIELD OF THE INVENTION

The invention relates to the field of non-destructive testing of a product or produce, e.g. by usage of ionizing radiation imaging. More specifically it relates to a method and system for inline product inspection, e.g. for automated quality control and/or selection, of an object, e.g. of a product or produce, such as a vegetable or a fruit, that is at least partially transparent to ionizing radiation, e.g. an x-ray transparent object. The invention further relates to the use of such method and/or system for quality control and/or selection of a quality object.

BACKGROUND OF THE INVENTION

Online detection of internal defects in products or produce, e.g. food items, using X-rays is known in the art for detecting defects that are easily discernable on radiographs. Particularly, X-ray imaging has become a valuable tool in many industrial branches to perform non-destructive tests for ensuring the quality of a product. Since most materials are translucent to X-rays, internal defects can be visualized without cutting open and damaging the product. For example, the use of two-dimensional X-ray radiographic imaging for non-destructively testing of the quality of products and/or detecting defects in products is known in the art, e.g. for inline inspection of food products in the food industry. Such a simple 2D radiographic projection, in which all features on the inside and the outside of the object are superimposed into one single image, may provide a fast way to visualize the interior of an object inline.

X-ray systems are commercially used for foreign body detection and, yet more limited, for the detection of certain common internal defects and unwanted properties in food systems such as insect presence in fruit, e.g. as disclosed by Haff et al in "X-ray detection of defects and contaminants in the food industry," *Sensing and Instrumentation for Food Quality and Safety,* 2(4), pp. 262-273, and by Jiang et al. in "An adaptive image segmentation algorithm for X-ray quarantine inspection of selected fruits," *Computers and Electronics in Agriculture,* 60(2), pp. 190-200. It is also known in the art to use X-ray imaging for automatic fish bone detection, e.g. as disclosed by Mery et al. in "Automated fish bone detection using X-ray imaging," *Journal of Food Engineering,* 105(3), pp. 485-492.

This approach, as known in the art, may however have several disadvantages. For example, density differences need to be large enough for defects and/or unwanted properties or objects to be visible in projection radiographs. This implies that this approach may not be useable in particular applications. Furthermore, custom algorithms may need to be developed for every type of defect or unwanted property that should be detected. This can prove to be very time consuming, certainly when taking into account that when imaged in different hardware setups, appearance of these defects can differ substantially.

To detect subtle features, a full three-dimensional CT reconstruction of the object may be needed, since particular internal defects cannot be discerned on projection images captured from a single point of view, or even by simultaneously evaluating a plurality of images corresponding to a plurality of complementary projection views, e.g. images corresponding to two or more projection views along mutually orthogonal projection axes. For example, in the food industry, some defects, such as browning disorders in fruit, inherently show low contrast with respect to their surroundings and can be very small.

Classical CT imaging methods imply that projections are taken from many angular positions around the sample, either by rotating the source-detector pair, e.g. in an arrangement commonly used for medical scanners, or by rotating the object sample while imaging the object, as may be known for industrial setups. This approach may have several implications when applied in online inspection system for inspecting an object conveyed by an inline transport system. For example, rotating the source-detector pair around a conveyor belt is impractical because of the high speeds that would be required to maintain an acceptable throughput speed of the conveyor belt. A high speed rotating gantry would require very expensive hardware, cause massive forces, imply additional safety constraints and make the hardware large and bulky. Furthermore, rotating the object sample over a large enough angular range for CT imaging, while moving on a conveyor belt, may also be undesirable because the rotation would also require a high speed and precise control, which is practically difficult to achieve. Even if these problems could be circumvented, an image processing algorithm may need to be developed for every type of defect or unwanted property that should be detected.

Due to cost, time and hardware constraints, a full 3D tomographic reconstruction is therefore difficult to achieve, or even infeasible, in an in-line application, e.g. in an inline sorting system for sorting x-ray transparent objects that are moving in an object stream, e.g. products or produce, such as a vegetable or a fruit, moving on a conveyor belt or similar conveying system. Moreover, the complexity of 3D CT imaging techniques as known in the art can have the disadvantages of being costly and complex and may substantially compromise the desired production line throughput when providing a sufficient image quality to ensure an acceptable defect detectability. For example, the trade-off between a high acquisition speed and a high contrast and resolution image, may be one of the main reasons why 3D X-Ray CT has not yet touched ground as an inspection tool in food industry. In other industrial branches, it may however be known to use CT in-line or at-line, for example as a metrology tool, for example using high throughput batch delivery systems or a continuous throughput conveyor belt system using a helical scanning approach. Nevertheless, such approaches remain quite costly and complex.

Attempts have been made to circumvent the problems mentioned above. For example, Rapiscan Systems developed an online CT-scanner for baggage inspection by combining a large number of source-detector pairs into one setup, e.g. the Rapiscan RTT™ 110 of Rapiscan Systems, Torrance, Calif. 90503 USA. This functioning yet expensive solution may reach speeds of 1500-1800 bags per hour, corresponding to a throughput speed of about 0.5 m/s, which may not be fast enough for a high volume, low value application such as the food industry.

In "Automated knot detection for high speed computed tomography on *Pinus sylvestris* L. and *Picea abies* (L.) Karst. using ellipse fitting in concentric surfaces," Computers and Electronics in Agriculture, 96 (2013), pp. 238-245, by Johansson et al., a method was disclosed that combines three-dimensional scanning and X-ray radiographs. However, a disadvantage of this method is that the data processing proposed in this prior art article is limited to the estimation of heartwood diameter and density in logs.

Another approach is to use the translation of an object on the conveyor belt to get projections in a limited angular range. However, a three-dimensional reconstruction from projection data in a limited angular range is not straightforward and may introduce large image artefacts. Research into this subject has been reported, e.g. by Iovea et al. in "Pure Translational Tomography—a Non-Rotational Approach for Tomographic Reconstruction," Proceedings of the $9^{th}$ European Conference on NDT ECNDT, Tu.1.4.1.

SUMMARY OF THE INVENTION

It is an object of embodiments of the present invention to provide good and efficient means and methods for inspection, classification and/or sorting of a moving object, e.g. a product or produce article moving along a predetermined path in a production, processing or packaging line.

The above objective is accomplished by a method and device according to the present invention.

It is an advantage of embodiments of the present invention that a quality object can be controlled and/or selected based on a model-based classification of internal defects or deficiencies of this object.

It is an advantage of embodiments of the present invention that a quality of an object can be classified, e.g. the quality of products or produce, by combining 3D-scanning and X-ray radiographs.

It is an advantage of embodiments of the present invention that a method or system in accordance with embodiments of the present invention can be applied to identify anomalies in a wide variety of objects, by applying a shape model of the object of interest as prior knowledge.

It is a further advantage of embodiments of the present invention that it is not required to develop custom algorithms specifically adapted for each type of defect to be detected.

It is an advantage of embodiments of the present invention that the amount of information that needs to be collected from an object, e.g. scanning and/or imaging data, can be relatively low, e.g. when compared to prior-art methods of similar performance in detecting defects, due to the incorporation of extensive prior knowledge about the objects under investigation in accordance with embodiments of the present invention, e.g. prior knowledge represented by a shape model and an average grey-value distribution.

It is an advantage of embodiments of the present invention that a simple inspection and/or sorting system can be implemented using simple and cheap hardware, e.g. relatively simple and cheap when compared to prior-art systems having similar performance. Furthermore, such implementation may not require any moving parts of the imaging and/or detection hardware, thus reducing costs compared to a full CT scanner.

It is an advantage of embodiments of the present invention that no tomographic reconstruction may be required, since classification can advantageously be performed by comparing two 2D images. It is a further advantage of embodiments of the present invention that a high throughput speed can be achieved, e.g. due to the relatively simple processing requirements. It is a yet further advantage that inline applications, such as automated quality control and/or selection of objects which are inline transported in a conveying system, are feasible due to the high throughput speeds achievable.

It is an advantage of embodiments of the present invention that multiple defects in an object need not be identified one by one, since such defects are detected simultaneously as a large deviation from a reference object.

Embodiments of the present invention may combine a model based classification, 3D-scanning and radiographic imaging for detecting internal defects discernible on radiographs and for advantageously detecting more subtle features by using a simulated radiograph of a full three-dimensional reconstruction image of a reference object.

In a first aspect, embodiments of the present invention relate to a non-destructive inspection method for inline inspection of an object, the non-destructive inspection method comprises moving, using an inline transport system, an object that is at least partially transparent to radiation of a predetermined radiation quality, e.g. an at least partially x-ray transparent object, along a predetermined path in between a radiation source for emitting radiation of the predetermined radiation quality, e.g. an ionizing radiation source, and an image detector, and through a field of view of a three-dimensional scanner. The method further comprises imaging the object using the image detector by detecting the radiation emitted by the radiation source and transmitted through the object to obtain a projection radiograph of an internal structure of the object. The method further comprises scanning an exterior surface of the object using the three-dimensional scanner to obtain three-dimensional scanning data of the object in the form of a point cloud representative of at least part of the exterior surface. The method further comprises fitting, using a processor, a shape model of the object to the point cloud to obtain a surface model of the exterior surface. The method also comprises creating, using the processor, a solid model of the surface model by taking a grey value distribution of a reference object into account. The method further comprises simulating, using the processor, a reference radiograph from the solid model, and comparing, using the processor, the reference radiograph with the projection radiograph to detect and/or measure internal deviations of the object with respect to the reference object. The step of creating the solid model and/or the step of simulating the reference radiograph takes a predetermined relative spatial configuration of the image detector, the radiation source and the three-dimensional scanner into account.

In a method in accordance with embodiments of the present invention, the scanning of the exterior surface may comprise generating a partial point cloud of the object, wherein the fitting comprises estimating the complete exterior surface and position of the object by fitting the shape model, wherein the creating of the solid model comprises filling in a volume defined by the surface model with the grey value distribution, the volume corresponding to the space coordinates of the object when imaged by the image detector, and wherein the simulating of the reference radiograph comprises simulating an imaging process of the solid model by forward projection using the predetermined spatial configuration of the image detector and radiation source in the space coordinates.

In a method according to embodiments of the present invention, the shape model and the grey value distribution may be created by acquiring CT scans of a plurality of reference object samples off-line and determining the shape model and the grey value distribution from the CT scans to be used as prior knowledge during the steps of fitting the shape model and creating the solid model in runtime.

In a method according to embodiments of the present invention, determining the shape model may comprise extracting a plurality of exterior surfaces, corresponding to the plurality of reference object samples, from the CT scans using image processing techniques, determining a plurality of corresponding spatial features in the plurality of exterior surfaces, determining a mean position and/or a variation in position of each of the plurality of corresponding spatial features, and determining the shape model taking the mean positions into account. The shape model may have free parameters that can be fitted to account for position of the object, orientation of the object and/or modes of variation of the object representative of the variations in position of the plurality of corresponding spatial features.

In a method according to embodiments of the present invention, the shape model may comprise a linear model that parametrizes a shape of the object as a linear combination of a mean shape and a plurality of modes of variation.

In a method according to embodiments of the present invention, the grey value distribution may be determined as a normalized reference volume image from the plurality of CT scans.

In a method according to embodiments of the present invention, determining the grey value distribution may further comprise applying a surface normalization scheme to derive the normalized reference volume image of a population of objects represented by the object samples independent of the shape of any individual object.

In a method according to embodiments of the present invention, determining the grey value distribution may comprise applying a normalized spherical sampling scheme to obtain the normalized reference volume image and creating the solid model may comprise applying a reversed normalized spherical sampling scheme to fit the normalized reference volume image to the surface model.

In a method according to embodiments of the present invention, the moving of the object may comprise moving the object inline on a conveyor belt.

In a method according to embodiments of the present invention, moving the object may move the object at a speed in the range of conveyer belt speeds of commercial installations, e.g. in the range of 0.1 m/s to 0.7 m/s.

In a method according to embodiments of the present invention, during the moving of the object along the predetermined path, the object may first pass through the three-dimensional scanner, and then, consequently, may pass through the field of view of the image detector.

In a method according to embodiments of the present invention, the object may be moved inline through a radiation field of each of a plurality of radiographic imaging systems, each comprising a radiation source, e.g. an ionizing radiation source, and an image detector, and through a scanning stage of at least one three-dimensional scanner.

In a method according to embodiments of the present invention, the radiation source, e.g. the ionizing radiation source, and the image detector may be statically arranged with respect to the inline transport system, e.g. mechanically fixed with respect to the inline transport system.

In a method according to embodiments of the present invention, the radiation source, e.g. the ionizing radiation source, and the image detector mat be fixed above a conveyor belt on which the object is transported.

In a second aspect, embodiments of the present invention relate to a non-destructive inspection system for inline inspection of an object. The non-destructive inspection system comprises a radiation source for emitting radiation of a predetermined radiation quality, e.g. an ionizing radiation source, and an image detector. The radiation source and the image detector form a radiographic imaging system for detecting radiation emitted by the radiation source and transmitted through an object that is at least partially transparent to radiation of the predetermined radiation quality, e.g. an at least partially x-ray transparent object, to provide a projection radiograph of an internal structure of the object. The system further comprises a three-dimensional scanner for scanning an exterior surface of the object to obtain three-dimensional scanning data of the object in the form of a point cloud representative of at least part of the exterior surface. The system also comprises an inline transport system for moving the object along a predetermined path in between the radiation source, e.g. the ionizing radiation source, and the image detector, and through a field of view of the three-dimensional scanner.

The system also comprises a processor adapted for: obtaining the projection radiograph from the image detector; obtaining the point cloud from the three-dimensional scanner; fitting a shape model of the object to the point cloud to obtain a surface model of the exterior surface; creating a solid model of the surface model by taking a grey value distribution of a reference object into account; simulating a reference radiograph from the solid model; and comparing the reference radiograph with the projection radiograph to detect and/or measure internal deviations of the object with respect to the reference object. The processor is further adapted for creating the solid model and/or simulating the reference radiograph by taking a predetermined relative spatial configuration of the image detector, the radiation source and the three-dimensional scanner into account.

In a system in accordance with embodiments of the present invention, the radiation source, e.g. the ionizing radiation source, may be a stationary radiation source and the image detector may be a stationary image detector.

A system in accordance with embodiments of the present invention may further comprise a plurality of stationary radiation sources, e.g. a plurality of stationary ionizing radiation sources, and stationary image detectors, forming a plurality of radiographic imaging systems.

In a system in accordance with embodiments of the present invention, the three-dimensional scanner may comprise a stationary light or laser source and a stationary light detector.

In a system in accordance with embodiments of the present invention, the radiation source may comprise an ionizing radiation source adapted for providing an x-ray exposure pulse to the object, and the image detector may comprise a digital image detector adapted for providing image data of the object corresponding to the x-ray exposure pulse as an input to the processor. The three-dimensional scanner may be adapted for providing light ray exposure to the object and may comprise a digital detector for providing data relating to the object obtained by the light ray exposure as an input to the processor.

In a further aspect, the present invention may also relate to the use of a method according to embodiments of the first aspect of the present invention for identifying anomalous objects transported on an transport line in an industrial process.

Particular and preferred aspects of the invention are set out in the accompanying independent and dependent claims. Features from the dependent claims may be combined with features of the independent claims and with features of other dependent claims as appropriate and not merely as explicitly set out in the claims.

These and other aspects of the invention will be apparent from and elucidated with reference to the embodiment(s) described hereinafter.

Figure 1:
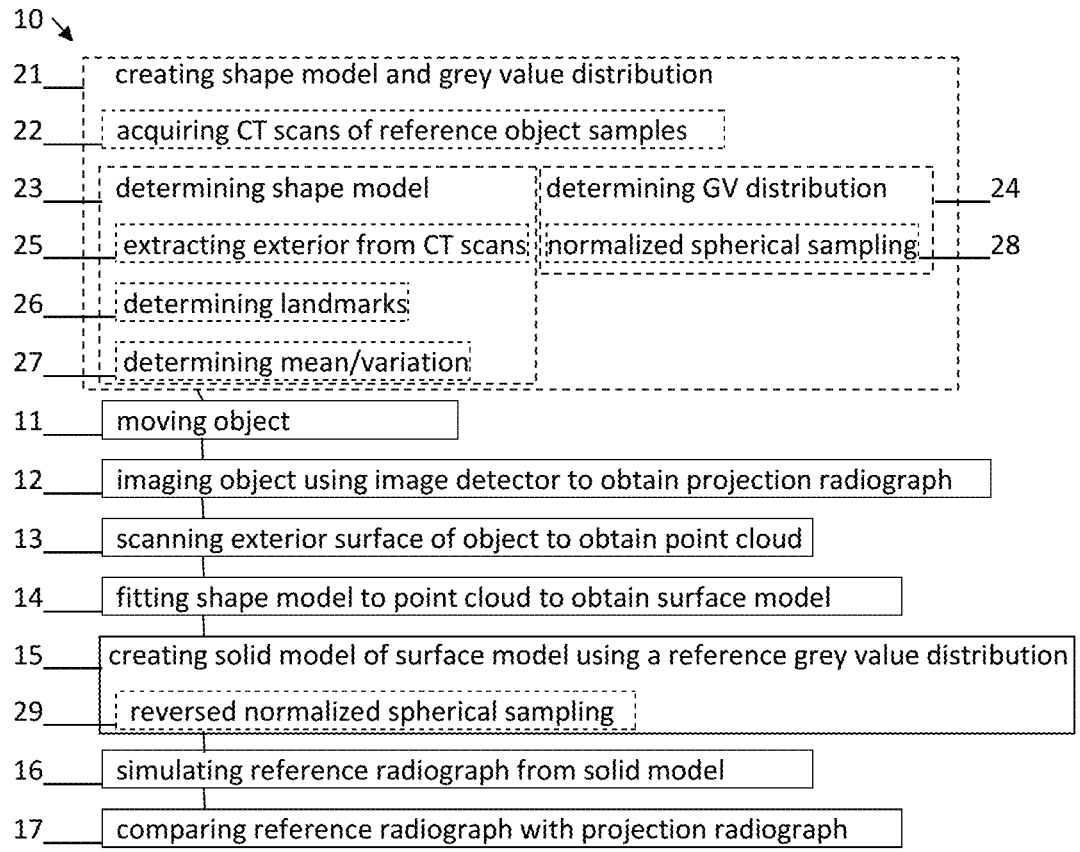
FIG. 1 illustrates an exemplary method in accordance with embodiments of the present invention.

The drawings are only schematic and are non-limiting. In the drawings, the size of some of the elements may be exaggerated and not drawn on scale for illustrative purposes.

Any reference signs in the claims shall not be construed as limiting the scope.

In the different drawings, the same reference signs refer to the same or analogous elements.

DETAILED DESCRIPTION OF ILLUSTRATIVE EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

Where in embodiments of the present invention reference is made to "grey value", reference is made to a digital pixel or voxel value. Particularly, it may refer to a scalar location-dependent value defined over a pixel or voxel coordinate system. The grey value of a pixel may be indicative of an amount of radiation received by a corresponding image detector, e.g. being proportional to, or having a monotonous functional relation to, an intensity or magnitude of radiation. For example, in volumetric images, the voxel grey value may be proportional to a local measure of attenuation of the radiation quality used for imaging by the material present at the voxel location. For example, for X-ray imaging, this voxel grey value may be proportional to the linear attenuation coefficient corresponding to the attenuation of this X-ray radiation in the voxel volume. For example, the voxel grey value may be normalized to Hounsfield units.

In a first aspect, the present invention relates to a non-destructive inspection method for inline inspection of an object. This non-destructive inspection method comprises moving, using an inline transport system, an object that is at least partially transparent to radiation of a predetermined quality, e.g. an x-ray transparent object, along a predetermined path in between a radiation source for emitting the radiation of this predetermined quality, e.g. an ionizing radiation source, and an image detector, for example a stationary radiation source and a stationary image detector, and through a field of view of a three-dimensional scanner. The method further comprises imaging the object using the image detector by detecting radiation emitted by the radiation source and transmitted through the object to obtain a projection radiograph of an internal structure of the object. The method also comprises scanning an exterior surface of the object using the three-dimensional scanner to obtain three-dimensional scanning data of the object in the form of a point cloud representative of at least part of the exterior surface.

The method further comprises fitting, using a processor, a shape model of the object to the point cloud to obtain a surface model of the exterior surface, and creating, using the processor, a solid model of the surface model by taking a grey value distribution of a reference object, e.g. a reference object without defects, into account. The method also comprises simulating, using the processor, a reference radiograph from the solid model and comparing, using the processor, the reference radiograph with the projection radiograph to detect and/or measure internal deviations, e.g. defects, of the object with respect to the reference object.

The step of creating the solid model and/or the step of simulating the reference radiograph takes a predetermined relative spatial configuration of the image detector, the radiation source and the three-dimensional scanner into account, e.g. such as to generate the reference radiograph in a coordinate system commensurate with the coordinate system of the projection radiograph obtained by imaging the object.

Embodiments of the present invention may relate to a method, and related system, using radiographic simulation, which may involve using ionizing radiation to detect a radiograph image for the inspection of internal defects in an object, in which additional features may be detected, e.g. more subtle features, in the object by comparing the acquired radiograph image with a simulated radiograph based on a full three-dimensional reconstruction image of a reference object, fitted to the geometrical constraints of a shape of the object detected by a three-dimensional scanner.

Figure 2:
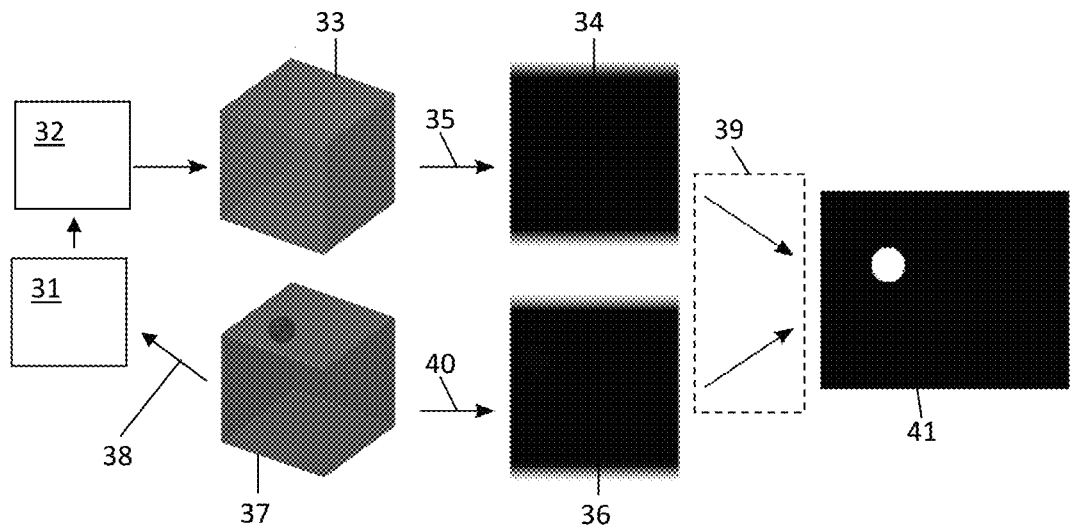
FIG. 2 illustrates a method in accordance with embodiments of the present invention.

A method in accordance with embodiments of the present invention may combine a three-dimensional scanner, e.g. comprising a laser line arrangement and/or multiple RGB cameras, with projection imaging, e.g. optical projection imaging of an object that is (at least partially) optically transparent or X-ray radiography of an object that is (at least partially) transparent to X-rays. Referring to FIG. 2, the working principles of a method in accordance with embodiments are schematically illustrated. In accordance with embodiments, a 3D scanner may produce a partial point cloud 31 by scanning a physical object 37. The partial point cloud 31 may then be used to estimate the complete outer surface 32 of the object by fitting a shape model, e.g. a statistical shape model. This surface model, e.g. the 'hollow' model of the object, may then be filled with a reference density distribution, e.g. a grey value distribution representative of an average object without defects, to produce a full volume 33 from which a radiography 34 may be simulated 35, e.g. using forward projection. This simulated radiography 34 may then be compared with a measured radiography 36, e.g. a measured radiography 36 obtained by projection imaging 40 of the physical object 37 using an X-ray system. Because the simulated radiography represents a perfect object without defects, observed differences 41 can be contributed to internal defects.

Referring to FIG. 1, an exemplary non-destructive inspection method 10 for inline inspection of an object in accordance with embodiments of the present invention is shown. For example, such method 10 may be a method for automatic real-time non-destructive inspection control, e.g. for detecting damage or a defect, of an object, e.g. a product or produce item, such as a vegetable or a fruit. The method may be adapted for non-destructive testing of a product or produce, e.g. by usage of ionizing radiation imaging. The method may be adapted for inline product inspection, e.g. for automated quality control and/or selection, of an object, e.g. of a product or produce, such as a vegetable or a fruit, that is at least partially transparent to ionizing radiation, e.g. an x-ray transparent object. However, embodiments of the present invention are not necessarily limited thereto, e.g. a method according to embodiments of the present invention may equally relate to the inline product inspection of an optically transparent object, e.g. a glass or transparent polymer object. Furthermore, the skilled person will understand that embodiments of the present invention may equally relate to other radiation qualities, such as electron beams, infrared radiation, ultraviolet radiation, hadron radiation, or acoustic waves.

This non-destructive inspection method 10 comprises moving 11 an object that is at least partially transparent to a predetermined radiation quality, e.g. an at least partially x-ray transparent object, along a predetermined path in between a radiation source, e.g. for emitting radiation having said radiation quality, and an image detector and through a field of view of a three-dimensional scanner. The field of view of the three-dimensional scanner refers to a spatial volume in which the scanner can operate, when an object is positioned in this spatial volume, to acquire scanning data of this object.

Particularly, the object may be moved along this predetermined path by an inline transport system, e.g. on a conveyor belt. In accordance with embodiments of the present invention, moving 11 the object may comprise moving the object inline on a conveyor belt. In accordance with embodiments of the present invention, moving 11 of the object may comprise moving the object at a speed in the range of 0.1 m/s to 0.7 m/s, e.g. on a conveyor belt.

The radiation source and image detector may form a projection imaging system, e.g. a radiography projection imaging system, e.g. an X-ray projection imaging system. The radiation source may for example comprise a Röntgen tube, a source of gamma radiation or a linear particle accelerator for generating X-ray radiation from a suitable target.

The ionizing radiation source and the image detector may be statically arranged with respect to the inline transport system. For example, the radiation source and the image detector may comprise a stationary radiation source and a stationary image detector. The ionizing radiation source and the image detector may for example be fixed above a conveyor belt whereon the object is transported.

The radiation source and the image detector may form a radiographic imaging system. In accordance with embodiments of the present invention, the object may be moved 11 inline through a radiation field of each of a plurality of radiographic imaging systems, each comprising an ionizing radiation source and an image detector, and through a scanning stage of at least one three-dimensional scanner. For example, the method may comprise combining the point clouds characterizing the exterior surface of the object obtained by multiple three-dimensional scanners at different locations along a transport line such as to improve a model fit of the shape model to the aggregated and/or filtered point cloud data. For example, the method may comprise imaging the object along different projection angles by multiple radiographic imaging systems, and performing the steps of simulating 16 a reference radiograph and comparing 17 the reference radiograph for each of the projection radiographs obtained for the different projection angles. Thus, a subtle defect that might be obscured in a first projection radiograph could be detected in another projection radiograph.

The method 10 further comprises imaging 12 the object using the image detector by detecting radiation emitted by the radiation source. This radiation is furthermore transmitted through the object when propagating from the source to the detector, e.g. such as to encode internal information regarding the object in spatial variations of the intensity of the radiation field over the detection surface of the detector. Thus, a projection radiograph is obtained of an internal structure of the object.

The method 10 further comprises scanning 13 an exterior surface of the object using a three-dimensional scanner to obtain three-dimensional scanning data of the object in the form of a point cloud representative of at least part of the exterior surface. For example, such three-dimensional scanner may comprise a laser line scanner or multiple RGB cameras. Such 3D scanner may be a device adapted for analyzing a physical object to collect data on its shape, such as to collect data that can be used to construct a partial or complete digital three-dimensional model of the object. The three-dimensional scanner may be an optical 3D scanner. The 3D scanner may comprise a non-contact active scanner, e.g. using light or ultrasound emissions. For example, the 3D scanner may comprise a time-of-flight 3D laser scanner, a triangulation-based 3D laser scanner or a conoscopic holographic laser scanner. The 3D scanner may comprise a structured light 3D scanner or a modulated light 3D scanner. The 3D scanner may also comprise a non-contact passive 3D scanner, such as a stereoscopic optical imaging system, a photometric imaging system, or a silhouette imaging system.

In a method in accordance with embodiments of the present invention, during the movement 11 of the object along the predetermined path, the object may first pass through the three-dimensional scanner. A processed point cloud may be produced by the three-dimensional scanner when the object passes the scanner. This point cloud may be incomplete, e.g. due to scan artefacts at an underside of the object where it is supported by a conveyor belt. Such incompleteness may be removed by estimating the complete outer shape of the object via a shape model, e.g. a statistical shape model, as described further hereinbelow. The object may then, consequently, pass through the field of view of the image detector where it is imaged 12.

This scanning 13 of the exterior surface may comprise generating a partial point cloud of the object, e.g. a partial point cloud representative of at least one exterior surface segment of the object that is positioned and oriented in a direct line of sight of the three-dimensional scanner. For example, the three-dimensional scanner may be adapted for generating a three-dimensional point cloud of points on the exterior surface of the object. For example, the three-dimensional scanner may comprise a laser line and an RGB camera system.

The method 10 further comprises fitting 14 a shape model of the object to the point cloud, using a processor, to obtain a surface model of the exterior surface. For example, this fitting may comprise estimating a complete exterior surface and position, e.g. a position and orientation, of the object by fitting the shape model to the point cloud, e.g. to the partial point cloud. By fitting the shape model, a complete surface, e.g. a hollow shape descriptor, may be obtained. This fitting may comprise determining a plurality of parameters of the shape model, e.g. determining a linear combination of components, a translation vector, a rotation vector and/or an affine transformation matrix. This fitting may comprise a search algorithm for finding a parameter combination corresponding to a maximum or a minimum of an objective function, e.g. such as to maximize the overlap between the shape model and the measured point cloud or to minimize a deviation between the shape model and the measured point cloud.

The method 10 also comprises creating 15 a solid model of the surface model, using the processor, by taking a grey value distribution, e.g. a normalized grey value distribution, of a reference object, e.g. a reference object without defects, into account. Creating the solid model may comprise filling in a volume defined by the surface model with the grey value distribution, in which this volume corresponds to the space coordinates of the object when imaged by the image detector. This volume may for example correspond to the space coordinates of the object due to the estimation of the position and/or orientation of the object in the fitting mentioned hereinabove.

For example, a normalized reference volume, e.g. derived from a CT dataset previously obtained from reference object samples, may be used to produce a volumetric image approximation of a reference object conforming to the shape model. The solid model may for example comprise a volumetric image, e.g. an approximation of a CT scan of the reference object, obtained by back-sampling for a normalized reference volume using an inversed surface normalization scheme. The reference object may be representative of a perfect instance of the object that passed under the three-dimensional scanner. This perfect instance may refer to a perfect instance having a matching shape to the scanned object, insofar achievable by the parametrization of the shape model, yet having no defects or abnormal deviations in internal structure to object samples used to construct the normalized reference volume.

The method 10 also comprises simulating 16 a reference radiograph from the solid model, using the processor. This step of simulating of the reference radiograph may comprise simulating an imaging process of the solid model by forward projection using the predetermined spatial configuration of the image detector and radiation source in the space coordinates of the object when imaged by the image detector. This reference radiograph may for example be simulated from the solid model, e.g. the volumetric image, using a forward projection method.

The step of creating 15 the solid model and/or the step of simulating 16 the reference radiograph takes a predetermined relative spatial configuration of the image detector, the radiation source and the three-dimensional scanner into account, e.g. such as to generate the reference radiograph in a coordinate system commensurate with the coordinate system of the projection radiograph obtained by imaging the object.

The method 10 further comprises comparing 17 the reference radiograph with the projection radiograph, using the processor, to detect and/or measure internal deviations, e.g. defects, of the object with respect to the reference object. For example, the measured projection radiograph may be compared to the simulated reference radiograph, in which any differences between the modelled and measured projection may be indicative for the presence of defects. Thus, if a substantial difference is detected, the object may be classified as defect. The result of this comparison may be brought to the attention of an operator, or may be fed as a signal to an automatic sorter to automatically remove the object from the inline transport line.

A method according to embodiments of the present invention may comprise obtaining the shape model and the grey value distribution in the form of a predetermined shape model and a predetermined grey value distribution as an input to be received by the processor.

A method according to embodiments of the present invention may comprise determining the shape model and the grey value distribution in a calibration phase, as described further hereinbelow.

In a method in accordance with embodiments of the present invention, the shape model and the grey value distribution may be created 21 by acquiring CT scans 22 of a plurality of reference object samples off-line, e.g. in an initial calibration phase before inline application of the method, and determining the shape model 23, e.g. by constructing a CAD model or applying a surface modelling method, and the grey value distribution 24 from these CT scans so as to be used as prior knowledge during the steps of fitting the shape model and creating the solid model in runtime, e.g. during inline application of the method. A method in accordance with embodiments of the present invention may comprise such initial step of creating 21 the shape model and the grey value distribution.

In a method in accordance with embodiments of the present invention, determining 23 the shape model may comprise determining a surface model by extracting 25 a plurality of exterior surfaces, corresponding to the plurality of reference object samples, from the CT scans using image processing techniques. For example, image processing techniques as known in the art may be applied to construct such exterior surface, e.g. image segmentation, edge detection, morphological filtering, image pre-processing and/or image post-processing. Such image processing may for example also comprise image registration of the plurality of CT scans, e.g. alignment of the images in position and orientation, to facilitate the detection of corresponding spatial features in the step of determining the corresponding spatial features discussed further hereinbelow.

Determining 23 the shape model may further comprise determining 26 a plurality of corresponding spatial features in the plurality of exterior surfaces, e.g. detecting each spatial feature in each of the plurality of exterior surfaces such that each spatial feature of the exterior surface of a sample object corresponds to a matching feature of the exterior surface of each other sample object. For example, such corresponding spatial features may be referred to as landmark features.

Determining 23 the shape model may further comprise determining 27 a mean position and/or a variation in position of each of the plurality of corresponding spatial features.

Determining 23 the shape model may also comprise determining the shape model taking the mean positions of each of the plurality of corresponding spatial features into account, e.g. taking the mean positions and variations in positions into account.

Thus, in accordance with embodiments of the present invention, the shape model may have free parameters that can be fitted to account for position of the object, orientation of the object and/or modes of variation of the object representative of the variations in position of the plurality of corresponding spatial features.

In a method in accordance with embodiments of the present invention, the shape model may comprise a linear model that parametrizes a shape of the object as a linear combination of a mean shape and a plurality of modes of variation. For example, this mean shape may correspond to a surface constructed using the mean positions of each of the plurality of corresponding spatial features, while the modes of variation may correspond to difference surfaces with respect to this mean shape, such that the linear span of the mean shape and the modes of variation encompasses the plurality of exterior surfaces determined from the CT scans.

In a method in accordance with embodiments of the present invention, the grey value distribution may be determined 24 as a normalized reference volume image from the plurality of CT scans. For example, determining 24 the grey value distribution may comprise applying a surface normalization scheme to derive the normalized reference volume image of a population of objects represented by the object samples, such that the grey value distribution is defined independent of the shape of any individual object. In accordance with embodiments of the present invention, the grey value distribution may be determined by applying a normalized spherical sampling scheme 28 to obtain the normalized reference volume image. For example, the grey value distribution may be derived from the CT dataset by performing a spherical sampling, e.g. from the center of each scan, normalized for the surface of the object sample, e.g. normalizing the radial distance to the surface to one for each radial sampling line. For example, a normalized spherical sampling scheme may be applied to each of the plurality of CT scans individually, and the resultant normalized reference volume images may be aggregated by applying a summary statistic over the set of normalized reference volume images, e.g. averaging the plurality of reference volume images.

In accordance with embodiments of the present invention, creating 15 the solid model may comprise applying 29 a reversed normalized spherical sampling scheme to fit the normalized reference volume image to the surface model. For example, the normalized reference volume image may define the common internal structure of several scanned reference object samples, regardless of their shape. Thus, any shape defined by the surface model of a particular object at hand can be filled with this normalized reference volume image by applying a reversed normalized spherical sampling scheme.

In a second aspect, the present invention also relates to a non-destructive inspection system for inline inspection of an object. The non-destructive inspection system comprises a radiation source, e.g. a radiation source for emitting radiation of a predetermined radiation quality, e.g. an ionizing radiation source, and an image detector, the source and detector forming a radiographic imaging system for detecting radiation emitted by the radiation source and transmitted through an object that is at least partially transparent to said predetermined radiation quality, e.g. an at least partially x-ray transparent object, to provide a projection radiograph of an internal structure of the object. The system further comprises a three-dimensional scanner for scanning an exterior surface of the object to obtain three-dimensional scanning data of the object in the form of a point cloud representative of at least part of the exterior surface. The system also comprises an inline transport system for moving the object along a predetermined path in between the ionizing radiation source and the image detector and through a field of view of the three-dimensional scanner.

A system in accordance with embodiments this second aspect of the present invention may implement a method in accordance with embodiments of the first aspect of the present invention. Therefore, features of a system in accordance with embodiments of the second aspect of the present invention may be clear to the person skilled in the art in view of the description provided hereinabove in relation to embodiments of the first aspect of the present invention. Likewise, features of a method in accordance with embodiments of the first aspect of the present invention may be clear to the person skilled in the art in view of the description provided hereinbelow in relation to embodiments of the second aspect of the present invention.

The non-destructive inspection system further comprises a processor adapted for obtaining the projection radiograph from the image detector and for obtaining the point cloud from the three-dimensional scanner. This processor is further adapted for fitting a shape model of the object to the point cloud to obtain a surface model of the exterior surface of the object. The processor is also adapted for creating a solid model of this surface model by taking a grey value distribution of a reference object into account. The processor is further adapted for simulating a reference radiograph from this solid model and for comparing the reference radiograph with the projection radiograph to detect and/or measure internal deviations of the object with respect to the reference object. The processor is also adapted for creating the solid model and/or simulating the reference radiograph by taking a predetermined relative spatial configuration of the image detector, the radiation source and the three-dimensional scanner into account.

Figure 3:
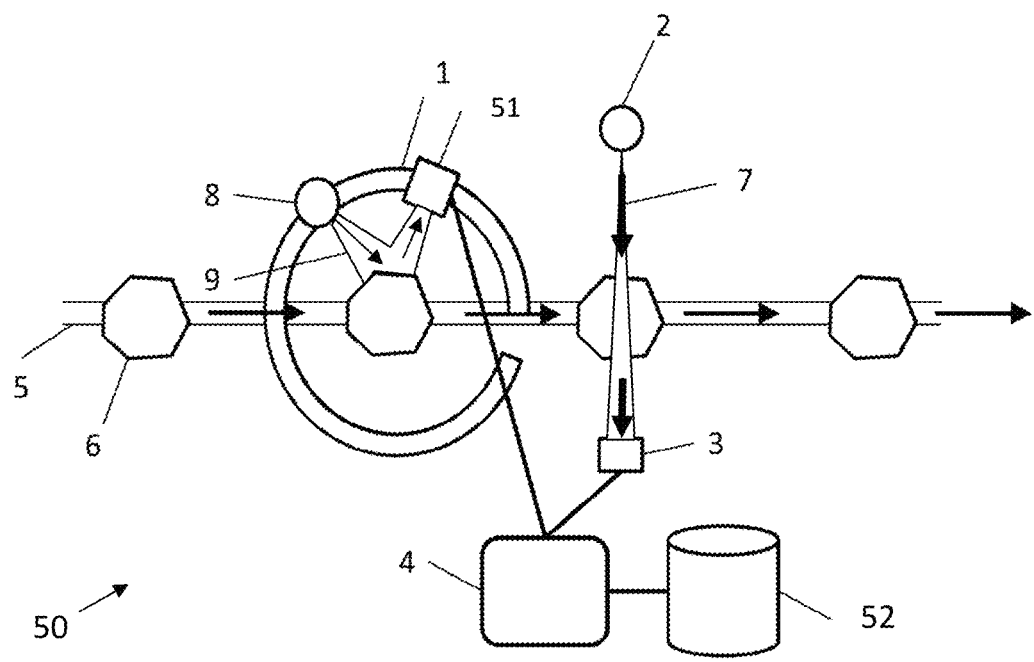
FIG. 3 illustrates an exemplary system in accordance with embodiments of the present invention.

Referring to FIG. 3, a non-destructive inspection system 50 for inline inspection of an object in accordance with embodiments of the present invention is shown. This non-destructive inspection system 50 may be a multimodal imaging device, e.g. combining a 3D scanner and an X-ray imaging device, for inline product inspection.

The non-destructive inspection system 50 comprises an ionizing radiation source 2 and an image detector 3, the source and detector forming a radiographic imaging system for detecting radiation emitted by the radiation source and transmitted through an at least partially x-ray transparent object to provide a projection radiograph of an internal structure of the object. The ionizing radiation source 2 may be a stationary radiation source for emitting radiation, e.g. a stationary X-ray source for emitting X-ray radiation. The image detector 3 may be a stationary image detector, e.g. a digital X-ray image detector, for capturing a projection image or radiograph of the object, e.g. a product or produce item, by detecting the radiation when transmitted through the object. The radiation source 2 may emit the ionizing radiation in the direction of a central point of a radiation-sensitive area of the image detector 3, e.g. may emit radiation in a mean direction, e.g. along a central beam axis direction 7, which may correspond to a mathematical line connecting the source focus to a central detector pixel location on the detector 3. The image detector 3 may consist of a line of detector pixels, or a two-dimensional array of detector pixels.

The radiation source 2 may emit radiation 7 in a predetermined cone angle such as to cover, preferably, substantially the entire radiation-sensitive area of the image detector 3. The source 2 may also provide a sufficiently high radiation flux such as to obtain a good signal to noise ratio when imaging the object 6 using the image detector 3.

The radiation source 2 may comprise a light source, e.g. a light source for emitting light in the infrared, near-infrared, optical and/or ultraviolet spectral range. The radiation source 2 may comprise an acoustic wave source.

The radiation source 2 may comprise a radioactive source, e.g. a gamma emitter, or an X-ray tube. The X-ray source may for example emit photons having energies in the range of 100 eV to 400 keV, e.g. in the range of 1 keV to 200 keV, for example in the range of 10 keV to 100 keV. However embodiments of the present invention may also relate to other types of radiation, e.g. particularly to types of radiation which can be transmitted through the object to be tested along a substantially linear trajectory, e.g. without significant reflection, refraction or diffraction of the radiation wave, while the absorption of the radiation in the object to be tested is neither very high nor very low, such that an acceptable contrast range can be achieved in the radiographic image. It is to be noted that the skilled person is well-aware of suitable radiation types, as known in the art, for radiation imaging of a specific object given its material properties and spatial dimensions, and has knowledge of corresponding sources and image detectors known in the art for such radiation type, which may thus be used as the radiation source 2 and the image detector 3 in accordance with embodiments of the present invention.

The image detector 3 is adapted for capturing a projection image or radiograph of the object 6 by detecting the radiation when transmitted through the object 6. The projection image may be obtained by means of an image detector 3 that is adapted for capturing, e.g. acquiring or detecting, parts of the projection image at different moments in time, e.g. acquiring the projection image non-simultaneously and/or in time frames corresponding to mutually disjunctive time frames of exposure. For example, the image detector may comprise a one-dimensional array of pixels, e.g. a line array, and a two-dimensional image may be collected while moving the object through the field of view of the radiographic imaging system.

The system 50 further comprises a three-dimensional scanner 1 for scanning an exterior surface of the object to obtain three-dimensional scanning data of the object in the form of a point cloud representative of at least part of the exterior surface. This three-dimensional scanner may be a 3D scanner device, e.g. comprising a laser line or multiple RGB cameras. The 3D scanner 1 may comprise one or more scanner sources 8 for emitting radiation 9 and one or more detectors 51 for capturing reflected radiation 9 from the object 6 while moving on the transport system 5. The scanner source 8 may comprise one or multiple radiation sources, e.g. comprising a laser and/or a light source. The scanner 1 may use laser triangulation; in which the detector 51 picks up laser light that is reflected off the object. By using trigonometric triangulation, using an accurately predetermined distance between the laser source and the detector, as well as an accurately predetermined angle between the laser and the sensor, the system may calculate the distance from the point on the object surface to the scanner. The 3D scanner 1 may also use a laser pulse-based technique, also known as time-of-flight scanning, based on a constant speed of light and a time period in which light from a laser source reaches the object and reflects back to the detector. The 3D scanner 1 may operate in a phase shift mode, in which the power of a laser beam is modulated, and the scanner is adapted to compare the phase of the laser light being sent out and the laser light at the detector after reflection off the object. The 3D scanner 1 may also comprise a conoscopic system, in which a laser beam is projected onto the surface and the immediate reflection along the same ray-path is transmitted through a conoscopic crystal and projected onto a detector. The scanner 1 may also use a structured light scanning method that projects a series of linear patterns onto the object and detects the edge of the projected pattern with a camera, and calculate the distance similarly.

The 3D scanner 1 may produce point cloud data of the three-dimensional surface topology of the object 6, which may be processed, e.g. stored and processed, in the processor 4 described further hereinbelow, e.g. stored and processed in a machine vision device. The point cloud may consist of a number of points, e.g. coordinates identifying such points, on the surface of the object 6, which allow a geometrical shape model to be fitted to the cloud such as to describe the surface of the object in a geometrically complete manner. To limit the number of points needed for fitting the geometrical shape, the processor 4, e.g. the machine vision device, may include a database of reference shapes that have been trained externally of the object category.

The system also comprises an inline transport system 5 for moving the object along a predetermined path in between the ionizing radiation source and the image detector and through a field of view of the three-dimensional scanner. The predetermined path thus traverses a field of view of the radiographic imaging system, e.g. such as to enable imaging of the object while moving along the predetermined path. The predetermined path also traverses a field of view of the three-dimensional scanner, e.g. such as to enable scanning of the object while moving along the predetermined path. This inline transport system may comprise a transport line for moving the object, e.g. the product or produce item, in between the radiation source and the image detector and, for example, under the 3D scanner.

The inline transport system 5 may comprise a transport line for moving the object 6 along a predetermined path through the 3D scanner 1 and in between the radiation source 2 and the image detector 3. For example, the transport line 5 may be adapted for moving a stream of objects 6 along the predetermined path, e.g. for moving each object 6 in the stream along the path.

The object 6 may thus be moved along a path in the 3D scanner 1 and in between the detector 3 and the radiation source 2, e.g. through a field of view observed by the detector 3, e.g. a digital X-ray detector, with respect to a radiation field, e.g. an X-ray beam, emitted by the radiation source 2, e.g. a diverging beam of X-rays emitted from a substantially point-like focal point of an X-ray tube and substantially directed toward a digital X-ray image detector.

This transport line may for example comprise a conveyor belt, e.g. a moving conveyor belt on which the product item is supported while being moved along the trajectory or an overhead conveyor from which the product item is hanging while being moved along the trajectory.

In operation, the object 6 to be inspected may travel along a trajectory formed by the predetermined path, in the volume of space between the scanner source 8 and the image detector 51, e.g. in such a way that images acquired by the image detector 51 can be used by the processor 4 to provide a sufficiently accurate 3D shape of the object, e.g. sufficiently accurate in view of product inspection requirements imposed by a specific application.

In operation, the object 6 to be inspected may then travel along a trajectory formed by the predetermined path, in the volume of space between the radiation source 2 and the radiation detector 3, e.g. in such a way that images acquired by the image detector 3 can be used by the processor 4 to provide a sufficiently accurate projection image of the object positioned in the same orientation on the transport line as when traveling through the 3D scanner, e.g. sufficiently accurate in view of product inspection requirements imposed by a specific application. Alternatively, a predetermined change of orientation and/or position of the object when scanned by the 3D scanner 1 and when imaged by the radiographic imaging system may be taken into account by the processor 4.

The non-destructive inspection system 50 further comprises a processor 4. This processor may comprise a machine vision device. Such machine vision device may comprise a 3D geometry reconstruction unit for determining the three-dimensional outer shape of the object, e.g. the product or produce item, based on data provided by the three-dimensional scanner data. The machine vision device may comprise a 3D volume rendering unit for generating an internal representation of the product, and a radiograph generation unit for determining a radiograph image of the internal representation of the product.

The processor 4 may have an associated memory for storing executable program code and/or data. The processor may comprise, or may be integrated in, a computer or digital processing workstation. The processor may comprise general purpose hardware for executing software code such as to instruct the processor to perform some or all tasks as described further hereinbelow. The processor may also comprise such software code, e.g. stored in a memory or on a data carrier readable by a data storage reader connected to, or part of, the processor. The processor may comprise hardware specifically adapted for performing some or all tasks further described hereinbelow, e.g. an application specific integrated circuit, a field programmable gate array device or a similar configurable hardware device known in the art. The processor may be provided with data representing an image of the object, e.g. via a connection to the radiographic imaging system, and with data representing a three-dimensional scan of the object, e.g. via a connection to the three-dimensional scanner. The processor may furthermore store these data in a memory associated with the processor. Optionally, an user interface having at least an output may be operably connected to the processor, such that a user can receive output from the processor and/or input commands to the processor.

The processor 4 is adapted for obtaining the projection radiograph from the image detector and for obtaining the point cloud from the three-dimensional scanner. This processor 4 may form a machine vision unit for complementing the imaging chain after the 3D scanning and radiographic image collection.

This processor is further adapted for fitting a shape model of the object to the point cloud to obtain a surface model of the exterior surface of the object. Thus, the point cloud may be used to compute a complete outer surface of the object by fitting a shape model (SM) of the object. Shape models may comprise any technical method to describe the three-dimensional shape of an object. The shape model may be rigid or deformable. A deformable model can be interpreted as a generalization of a rigid representation. Thus, methods and systems in accordance with embodiments of the present invention may relate to either deformable or rigid models, e.g. when applied to rigid models the degree of freedom related to shape deformation will be absent. An example of rigid models are those resulting from conventional computer aided design (CAD). Such CAD models may be widely available for products in production environments, where substantially identical products need to be inspected. In this case, the 3D scanner will serve to assess the exact translational and rotational position of the product, e.g. on a conveyor, based on the measured point cloud. An example of deformable shape models are statistical shape models (SSM), such as those described by Heimann et al. in "Statistical shape models for 3D medical image segmentation: a review," *Medical Image Analysis,* 13(4), pp. 543-63. The contents of this referenced document is hereby incorporated by reference. In embodiments according to the present invention, the shape model may comprise a SSM obtained by principal component decomposition, e.g. resulting in a mean shape for the object population and possible deviations thereof. However, in other embodiments according to the present invention, other methods for defining the shape model may be applied, e.g. parametric methods such as parametric methods based on spherical harmonics. In case of a deformable shape model, the 3D scanner 1 may aid in assessing the translational and rotational position of the object, and additionally, may serve to determine a best fitting instance of a model population to the object shape of the object 6.

Figure 4:
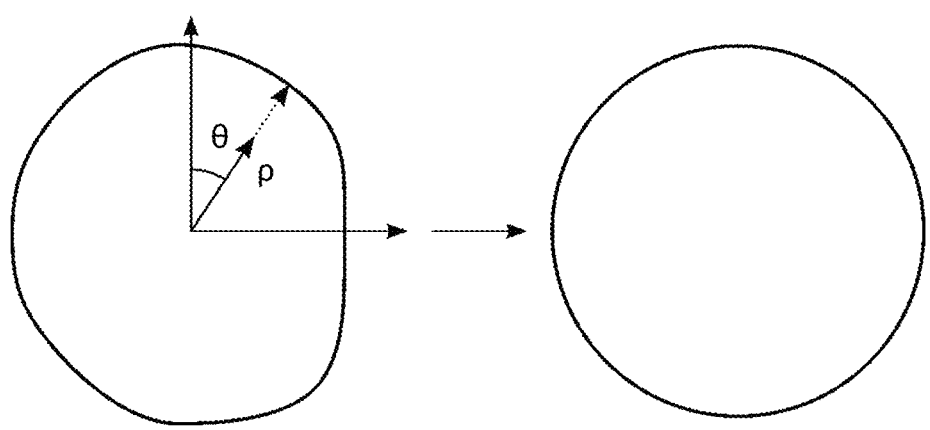
FIG. 4 illustrates a surface normalization approach using spherical sampling that relates to embodiments of the present invention.

The processor 4 is also adapted for creating a solid model of this surface model by taking a grey value distribution of a reference object into account. For example, the processor 4, e.g. the machine vision unit, may fill the 3D shape model of the object 6 to obtain an internal representation or volumetric image of the object. In accordance with embodiments of the present invention, an internal representation of the object may be provided by generating a distribution inside the object representation that provides values of a physical property of the object that influences the interaction of the radiation applied by the ionizing radiation source 2 with the object. In one embodiment, this property can be a density that determines the absorption of X-ray radiation energy. In one example, this value distribution can be spatially uniform inside the object, e.g. the entire 3D model of the object is filled with the same value. This may, for example, be a suitable option for objects composed of a material having a uniform density. In another example, this distribution is normalized for the surface by applying a spherical sampling from the centre of the shape where the radius is normalized for the distance to the surface, as illustrated in FIG. 4. In yet another example, this distribution may be normalized by applying a reversible non-rigid registration to a reference sample.

The value distribution may furthermore be not uniform, but position dependent. In embodiments according to the present invention, the object representation may be subdivided into discrete volume elements, referred to as voxels, which may be assigned different values. This value distribution may represent internal structures in the object, e.g. in a case where the object consists of parts made of different materials that have a different density, e.g. possibly including the presence of internal cavities.

Such value distribution may be obtained from a prior knowledge database 52 containing normalised object reference descriptions, e.g. descriptors in a machine-readable and machine-parsable form, including, for example, the 3D shape and internal representation and possibly other statistics. This database may be acquired by taking 3D volumetric scans of a number of exemplary object samples, e.g. product items without defects. Such volumetric scans may for example be obtained using a tomography imaging and reconstruction system, and may be used to create a model of the object under consideration, to be used as prior knowledge during runtime.

The value distribution in the database may be normalized for the shape population of the object, e.g. as depicted in FIG. 4, and may be back-sampled into the measured instance of the described shape, e.g. the fitted shaped model forming a surface model of the scanned object, thus resulting in a volumetric representation, e.g. a volumetric image, of the object under investigation with reference internal properties. Methods to obtain surface normalised volume data may include surface normalized spherical sampling schemes and non-rigid fluid based registrations to a reference volume. The normalized sampling scheme may allow for deriving a mean spatial density distribution of a population of samples, regardless of the shape of the individual samples.

The processor 4 is further adapted for simulating a reference radiograph from this solid model. The processor is also adapted for creating the solid model and/or simulating the reference radiograph by taking a predetermined relative spatial configuration of the image detector, the radiation source and the three-dimensional scanner into account. The processor 4, e.g. the machine vision unit, may produce a reference projection image or radiograph of the filled reference object or product item using the measured and filled 3D shape model and predetermined characteristics of the radiation source 2 and detector 3, using suitable projection algorithms. The predetermined characteristics may include source and detector polychromatic behaviour, source and detector position, detector size and pixel size, source focal spot size etc. Suitable projection algorithms may include line tracing and integration algorithms for determining the amount of radiation energy passing through the product item.

The processor 4 is also adapted for comparing the reference radiograph, e.g. obtained by simulation, with the projection radiograph, e.g. obtained by measurement performed by the radiographic imaging system, to detect and/or measure internal deviations of the object with respect to the reference object.

This processor 4, e.g. the machine vision unit 4, may further be programmed for applying machine vision algorithms for the detection of defects in the imaged object. For example, the processor 4 may comprise a computer or cluster of computers programmed for applying such machine vision algorithms. The images may be analyzed to extract information about possible defects by combining, such as subtracting and/or analyzing, the reference projection image to the actual image captured by the detector 3. The reconstruction and computer vision analysis may be addressed with suitably scaled computing power and well-developed algorithms, as are available in the state of the art and can be readily applied by the skilled person. However, it is to be noted that a convenient selection of suitable projection and defect detection algorithms may have an impact on signal-to-noise tolerances in the imaging chain. Therefore, it is a further advantage of embodiments of the present invention that an improvement of quality tolerances in reference radiographs and/or detection can be used to increase the throughput of the system 50 without requiring extensive reconfiguration of the system 50.

For example, the reference radiograph may be compared to the projection radiograph, e.g. using an image difference metric, to detect an object deviating from the sample population represented by the shape model and the grey value distribution, e.g. by applying a threshold criterion on the image difference metric. However, if an abnormality is so detected, further machine vision algorithms may be engaged to further classify or determine the nature of the abnormality. It is an advantage that, for an inline transport system feeding a stream of objects through the imaging components that have a low defect rate, complex machine vision algorithms to classify or determine the nature of defects need only be activated infrequently. Thus, a simple screening can be provided in accordance with embodiments of the present invention that may not unduly substantially impede the throughput of such inline system.

For example, the non-destructive inspection system 50 may be an object selection system or apparatus comprising a processor, e.g. having an associated memory for storing programs and data, of a computer or workstation. Such object selection system or apparatus may further comprise a device that combines a 3D-scanner, e.g. using a laser line and/or multiple RGB cameras, and a X-ray radiography system. An output of this device may be coupled to an input of the processor of the computer or workstation. In such object selection system or apparatus, which combines X-ray radiographs, 3D-scanning and processing, the X-ray radiography system may provide x-ray source exposure pulses to the object and may provide image data of the object corresponding to such exposure pulse, e.g. via an energizable (digital) detector, to the input of the processor. The processor may be energizable to acquire each image data set. The 3D-scanner may provide light ray exposure to the object and may provide scanning data of the object corresponding to such exposure pulse, e.g. via an energizable (digital) detector, to the input of the processor, which is energizable to acquire each scanning data set. The object selection system or apparatus may furthermore be characterised in that the processor, when energized, fits a shape model and a density model to partial point clouds as captured by classic 3D sensing systems. In an embodiment of the present invention, the processor of the above described system may process the 3D scanning data into a point cloud, estimate the outer surface thereof by fitting a shape model (SM) to create a surface model of the object, use a surface normalized grey value distribution to fill the surface model to produce a full volume image of a reference object conforming to the shape of the object, e.g. a perfect reference object having no defects or abnormalities yet the same or similar shape, simulate a radiograph from this solid model obtained by filling in the surface model and analyze the differences between the radiographic image, e.g. the measured radiograph of the object, and the simulated radiograph of the perfect full volume image to calculate or display the internal defects of the object.

It is an advantage of embodiments of the present invention that anomalous objects may be identified by using a shape model and a grey value distribution as prior knowledge, such that a system in accordance with embodiments of the present invention can be easily adapted to different types of object by providing a suitable shape model and grey value distribution as prior knowledge.

Further hereinbelow, examples relating to embodiments of the present invention are provided. These examples should not be construed as limiting the scope of the present invention in any way, but are merely provided for informative purposes, e.g. to assist the skilled person in understanding working principles of embodiments of the present invention and to aid the skilled person in reducing the invention to practice.

In a first example, a training dataset is used to train the models used in embodiments according to the present invention. This training dataset was acquired by taking CT scans of a number of samples without defects on an industrial CT-system. In this example, the model comprises two parts: an outer shape and an internal density distribution.

Figure 5:
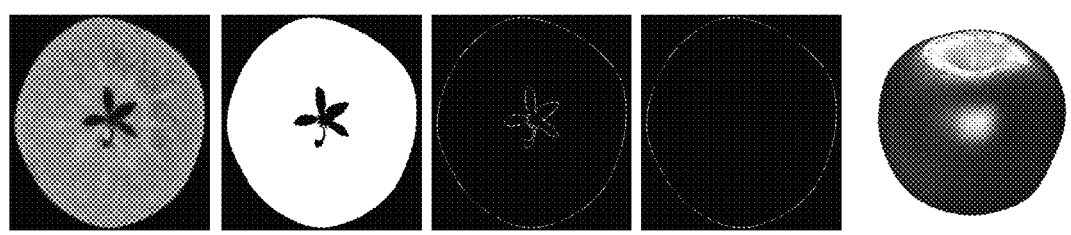
FIG. 5 shows an example of basic image processing techniques that can be applied in a calibration step of a method in accordance with embodiments of the present invention.
Figure 6:
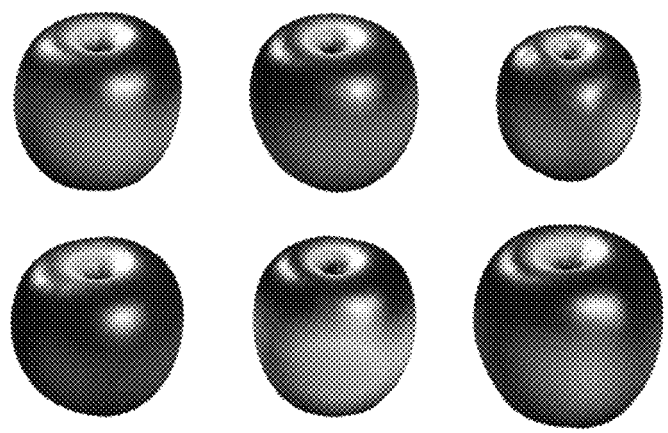
FIG. 6 shows a parameterized shape in accordance with a shape model that can be applied in embodiments of the present invention.

After reconstruction of the CT scans, the outer shape of the scanned samples was extracted using basic image processing techniques such as segmentation, edge detection and pre- and post-processing, illustrated in FIG. 5. Corresponding points, e.g. landmarks, on all these surfaces were extracted, after which the variation in position of every point was be determined. The result of this process is a mean shape with various modes of variation, which represent the variability of the shape. Any shape in the population represented by the acquired samples may then be reconstructed through a linear combination of the mean shape and its modes of variation, e.g. using a method as disclosed by Heimann et al., previously referred to hereinabove, and herewith incorporated by reference. FIG. 6 shows various random apple shapes generated with the method described above.

The inside of the object was modelled with a mean spatial density distribution derived from the CT-dataset. This was done by performing a spherical sampling from the centre of each scan, normalized for the surface of the sample, as illustrated by FIG. 4. Such normalized sampling scheme allows for deriving the mean spatial density distribution of a population of samples, regardless of the shape of the individual samples. This means that the average interior of all scanned samples is described, regardless of their shape. This also means that any shape as obtainable by varying the parameters of the shape model as described hereinabove can be filled with this reference distribution by applying a reversed normalized spherical sampling scheme.

Figure 7:
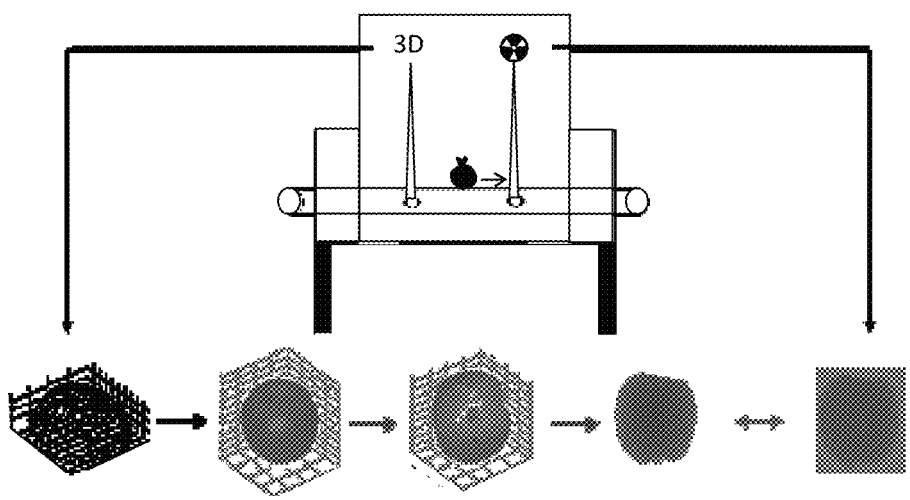
FIG. 7 illustrates a runtime process in an example relating to embodiments of the present invention.

During runtime, the object may first pass through a 3D-scanner. This 3D-scanner can be based on a laser line, RGB cameras or any other system that produces a 3-dimensional point cloud. The resulting point cloud may be incomplete, for example because such systems commonly may not be able to detect the underside of an object. In combination with the shape model that was constructed during training, as described hereinabove, it can however be used to approximate the complete outer shape of the object. Once this—hollow—shape is known, it may be combined with the mean spatial density distribution by back-sampling this distribution, e.g. using a reversed normalized sampling scheme. The resulting 'filled' shape may be an approximation of a CT-scan of a perfect instance of the object that passed under the 3D-scanner, e.g. having the same or very similar shape but under the assumption that no defects are present in it. An X-ray radiography may be simulated by calculating a forward projection from this model. In a final step, the object passes through an X-ray radiography scanner. The resulting 'measured' radiography is compared with the 'simulated' one. Because the modelled object is perfect, e.g. without any defects, any differences between the modelled and measured projection indicate the presence of defects, thus allowing it to be classified as 'defected' or 'not conformant'. This runtime process is schematically illustrated in FIG. 7. Furthermore, the processing flow is schematically illustrated in FIG. 8.

FIG. 2 shows an optimization and simulation relating to embodiments of the present invention. This illustration exemplifies a setup applied to a rigid cubic sample with a spherical abnormality with a 10% density difference. The measured point cloud and provided 3D model are used to assess the rotational and translational position of the sample. When combined with the prior knowledge density distribution, a perfect instance of the object is obtained, from which a radiograph is simulated. This is then compared with a measured radiograph, to identify the abnormality.

Figure 8:
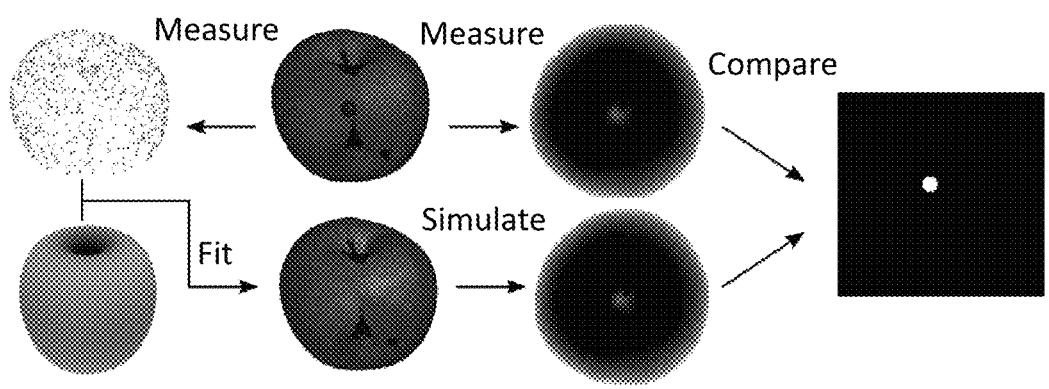
FIG. 8 further illustrates the process flow of said example, relating to embodiments of the present invention.

FIG. 8 shows a similar optimization and simulation relating to embodiments of the present invention. This illustration shows a setup applied to a sample with a complex variable shape: an apple with a spherical abnormality with a 10% density difference with respect to the surrounding tissue. The sample passing through the setup results in a measured point cloud and a measured radiograph. The provided deformable shape model is combined with the point cloud and the mean density distribution to result in a perfect instance of the sample. From this perfect instance a radiograph is simulated, which is compared with the measured radiograph to identify the abnormality.

Figure 9:
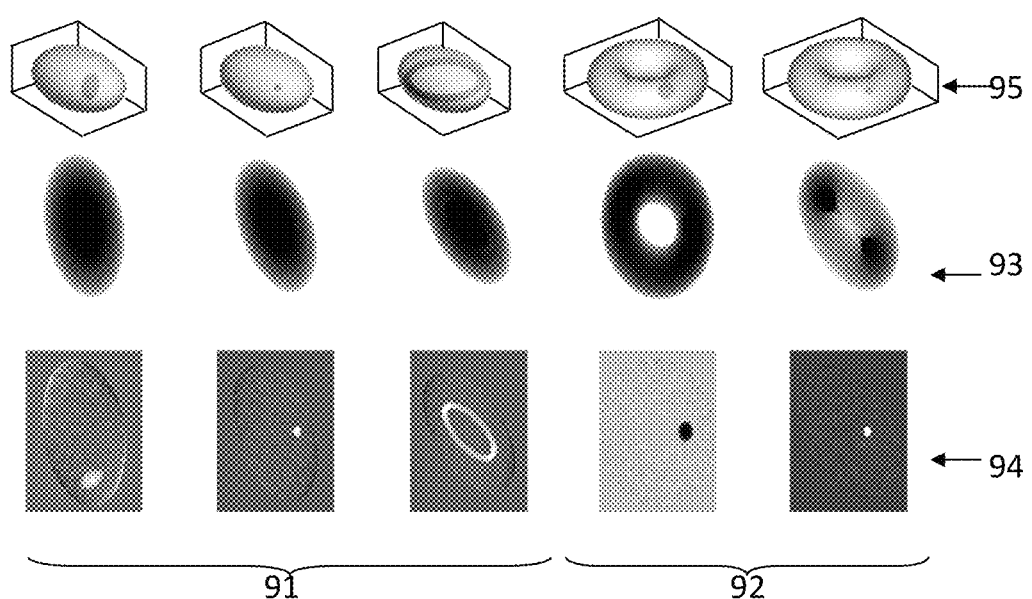
FIG. 9 illustrates exemplary shape—defect combinations relating to an example for demonstrating embodiments of the present invention.

Another example for illustrating features and advantages of a method in accordance with embodiments of the present invention is shown in FIG. 9. FIG. 9 shows two different shapes, respectively an ellipsoid 91 and a toroid 92, combined with different types of defects, e.g. ellipsoidal, spherical and toroidal defects, with contrasting density. On the second row 93 of the figure, X-ray radiographs are shown taken from a random orientation of the objects. On the third row 94, the difference between the measured radiograph, e.g. shown on the second row 93, and the simulated radiograph obtained by using the 3D shape without defect, e.g. shown on the first row 95, is depicted. While it may be very difficult to distinguish the defects in the measured radiographs, these defects may be easily visible on the comparison images, e.g. illustrated in the third row 94, e.g. in such way that image processing could be easily performed.

In this example, 1250 samples with varying defect intensities and 1250 samples without defects were processed by a method in accordance with embodiments of the present invention. A 10-fold cross validated naïve Bayesian classification using the simple sum of all pixels values in the comparison images could correctly identify 97.4% of the samples as containing a defect or not. However, to achieve the same result in accordance with methods known in the art, separate image processing algorithms, e.g. including thresholding, might have to be developed for each shape—defect combination to detect defects in the measured radiographs.

The invention claimed is:

1. A non-destructive inspection method for inline inspection of an object, the non-destructive inspection method comprising:
    moving, using an inline transport system, an object, that is at least partially transparent to radiation of a predetermined radiation quality, along a predetermined path in between a radiation source, for emitting radiation of said predetermined radiation quality, and an image detector, and through a field of view of a three-dimensional scanner;
    imaging said object using the image detector by detecting said radiation emitted by the radiation source and transmitted through said object to obtain a projection radiograph of an internal structure of said object;
    scanning an exterior surface of said object using the three-dimensional scanner to obtain three-dimensional scanning data of said object in the form of a point cloud representative of at least part of said exterior surface;
    fitting, using a processor, a shape model of said object to said point cloud to obtain a surface model of said exterior surface;
    creating, using said processor, a solid model of said surface model by taking a grey value distribution of a reference object into account;
    simulating, using said processor, a reference radiograph from said solid model; and
    comparing, using said processor, said reference radiograph with said projection radiograph to detect and/or measure internal deviations of said object with respect to the reference object,
    wherein said step of creating the solid model and/or said step of simulating said reference radiograph takes a predetermined relative spatial configuration of said image detector, said radiation source and said three-dimensional scanner into account.

2. The method according to claim 1, wherein said scanning of said exterior surface comprises generating a partial point cloud of said object,
    wherein said fitting comprises estimating the complete exterior surface and position of the object by fitting said shape model,
    wherein said creating of the solid model comprises filling in a volume defined by said surface model with said grey value distribution, said volume corresponding to the space coordinates of the object when imaged by the image detector, and
    wherein said simulating of said reference radiograph comprises simulating an imaging process of the solid model by forward projection using said predetermined spatial configuration of the image detector and radiation source in said space coordinates.

3. The method according to claim 1, wherein said shape model and said grey value distribution are created by acquiring CT scans of a plurality of reference object samples off-line and determining the shape model and the grey value distribution from said CT scans to be used as prior knowledge during said steps of fitting the shape model and creating the solid model in runtime.

4. The method according to claim 3, wherein determining said shape model comprises:
    extracting a plurality of exterior surfaces, corresponding to said plurality of reference object samples, from said CT scans using image processing techniques,
    determining a plurality of corresponding spatial features in said plurality of exterior surfaces,
    determining a mean position and/or a variation in position of each of said plurality of corresponding spatial features, and
    determining the shape model taking said mean positions into account, said shape model having free parameters that can be fitted to account for position of the object, orientation of the object and/or modes of variation of the object representative of said variations in position of said plurality of corresponding spatial features.

5. The method according to claim 4, wherein said shape model comprises a linear model that parametrizes a shape of the object as a linear combination of a mean shape and a plurality of modes of variation.

6. The method according to claim 3, wherein said grey value distribution is determined as a normalized reference volume image from said plurality of CT scans.

7. The method according to claim 6, wherein determining said grey value distribution further comprises applying a surface normalization scheme to derive the normalized reference volume image of a population of objects represented by said object samples independent of the shape of any individual object.

8. The method according to claim 7, wherein determining said grey value distribution comprises applying a normalized spherical sampling scheme to obtain the normalized reference volume image and wherein creating said solid model comprises applying a reversed normalized spherical sampling scheme to fit the normalized reference volume image to said surface model.

9. The method according to claim 1, in which said moving of said object comprises moving said object inline on a conveyor belt.

10. The method according to claim 1, whereby said moving of said object moves said object at a speed in the range of 0.1 m/s to 0.7 m/s.

11. The method according to claim 1, wherein, during said moving of said object along said predetermined path, said object first passes through said three-dimensional scanner, and then, consequently, passes through the field of view of the image detector.

12. The method according to claim 1, wherein said object is moving inline through a radiation field of each of a plurality of radiographic imaging systems, each comprising an ionizing radiation source and an image detector, and through a scanning stage of at least one three-dimensional scanner.

13. The method according to claim 1, wherein said radiation source and said image detector are statically arranged with respect to said inline transport system.

14. The method according to claim 13, in which the radiation source and the image detector are fixed above a conveyor belt whereon said object is transported.

15. The use of a method according to claim 1 for identifying anomalous objects transported on an transport line in an industrial process.

16. A non-destructive inspection system for inline inspection of an object, the non-destructive inspection system comprising:
   a radiation source and an image detector forming a radiographic imaging system for detecting radiation emitted by the radiation source and transmitted through an object that is at least partially transparent for said radiation, to provide a projection radiograph of an internal structure of said object;
   a three-dimensional scanner for scanning an exterior surface of said object to obtain three-dimensional scanning data of said object in the form of a point cloud representative of at least part of said exterior surface;
   an inline transport system for moving the object along a predetermined path in between the radiation source and the image detector and through a field of view of the three-dimensional scanner; and
   a processor adapted for:
   obtaining said projection radiograph from said image detector,
   obtaining said point cloud from said three-dimensional scanner,
   fitting a shape model of said object to said point cloud to obtain a surface model of said exterior surface,
   creating a solid model of said surface model by taking a grey value distribution of a reference object into account,
   simulating a reference radiograph from said solid model; and
   comparing said reference radiograph with said projection radiograph to detect and/or measure internal deviations of said object with respect to the reference object,
   wherein the processor is further adapted for creating said solid model and/or simulating said reference radiograph by taking a predetermined relative spatial configuration of said image detector, said radiation source and said three-dimensional scanner into account.

17. The system according to claim 16, wherein said radiation source is a stationary radiation source and said image detector is a stationary image detector.

18. The system according to claim 17, wherein said system further comprises a plurality of stationary radiation sources and stationary image detectors forming a plurality of radiographic imaging systems.

19. The system according to claim 16, wherein said three-dimensional scanner comprises a stationary light or laser source and a stationary light detector.

20. The system according to claim 16, wherein said radiation source is adapted for providing an x-ray exposure pulse to said object and said image detector is a digital image detector adapted for providing image data of said object corresponding to said x-ray exposure pulse as an input to said processor, and
   wherein said three-dimensional scanner is adapted for providing light ray exposure to said object and comprises a digital detector for providing data relating to said object obtained by said light ray exposure as an input to said processor.

* * * * *